United States Patent [19]

Miyata et al.

[11] Patent Number: 4,592,864
[45] Date of Patent: Jun. 3, 1986

[54] AQUEOUS ATELOCOLLAGEN SOLUTION AND METHOD OF PREPARING SAME

[75] Inventors: Teruo Miyata, Tokyo; Toshio Taira, Kawasaki, both of Japan

[73] Assignee: Koken Co., Ltd., Tokyo, Japan

[21] Appl. No.: 634,253

[22] Filed: Jul. 25, 1984

[30] Foreign Application Priority Data

Jul. 27, 1983 [JP] Japan ................. 58-137007

[51] Int. Cl.$^4$ .............. A61K 37/00; C07K 15/20
[52] U.S. Cl. ....................... 530/356; 514/21; 514/801; 106/124
[58] Field of Search ............ 260/123.7; 106/124, 106/157, 161; 514/21, 801

[56] References Cited

U.S. PATENT DOCUMENTS

| | | | |
|---|---|---|---|
| 3,949,073 | 4/1976 | Daniels et al. | 424/359 |
| 4,164,559 | 8/1979 | Miyata et al. | 424/14 |
| 4,223,984 | 9/1980 | Miyata et al. | 351/160 |
| 4,233,360 | 11/1980 | Luck et al. | 428/310 |
| 4,424,208 | 1/1984 | Wallace et al. | 424/177 |
| 4,440,750 | 3/1984 | Glowacki et al. | 424/95 |

OTHER PUBLICATIONS

Bauer, *Clinical Laboratory Methods*, C. V. Mosby Company, St. Louis, 1982, pp. 532–533.

*Primary Examiner*—John Kight
*Assistant Examiner*—Nathan M. Nutter
*Attorney, Agent, or Firm*—Armstrong, Nikaido, Marmelstein & Kubovcik

[57] ABSTRACT

An aqueous atelocollagen solution, which can be injected into living bodies as a medical material, has a pH value in the range from about 6.5 to about 8.0 and an osmolality in the range from about 250 to about 320 mOsm/KgH$_2$O, and contains a phosphate buffer solution, or glucose and a phosphate buffer solution, as an agent to adjust pH and osmolality within the ranges specified above. This aqueous atelocollagen solution can be prepared by dissolving atelocollagen in an aqueous acidic solution and adding the above-mentioned pH- and osmolality-adjusting agent to the resulting solution in such an amount as to adjust pH and osmolality of the final solution within the ranges mentioned above.

8 Claims, No Drawings

AQUEOUS ATELOCOLLAGEN SOLUTION AND METHOD OF PREPARING SAME

BACKGROUND OF THE INVENTION

1. Field of the Invention

This invention relates to an aqueous solution of atelocollagen and the method of preparing the same.

The aqueous atelocollagen solution of this invention can be injected into living bodies without any trouble; it is sufficiently fluid to allow easy injection, for example, through a fine syringe needle and is capable of regenerating collagen fiber when it becomes equilibrated with biological conditions.

2. Description of the Prior Art

Collagen is the major protein which constitutes the connective tissues of animals, such as the skin, blood vessels, cornea, tendons, bones and teeth, having a molecular weight of approximately 300,000. It has a rod-like molecular structure of helical configuration consisting of three polypeptide chains, about 3,000 Å in length and about 15 Å in diameter.

Collagen molecules, which are biochemically synthesized by collagen-producing cells in living bodies, are incorporated in the surrounding collageous fiber tissue and gradually change into insoluble collagen through intermolecular crosslinking.

This insoluble collagen cannot be extracted by dilute aqueous acid solutions. The juvenile collagen immediately after formation, on the other hand, can be extracted by dilute aqueous acid solutions because of the absence of crosslinks, even when it is present on or in the surrounding collagen fiber tissue. This acid-extractable collagen is called soluble collagen.

The insoluble collagen, if treated with a proteolytic enzyme, such as pepsin, undergoes fission at the intermolecular crosslinks and becomes soluble in dilute acids. During this treatment with pepsin, the telopeptide groups at both terminals of each collagen molecule are digested, thus leaving collagen with no telopeptide terminal ends. The collagen thus released is called atelocollagen. Since the telopeptide moiety is primarily responsible for antigenicity of collagen, atelocollagen has little antigenicity if any, which makes it very suitable for use as a medical material.

Use of purified collagen as a medical material for therapeutical applications has been expanding and becoming diversified. For example, purified collagen is employed as local hemostatics in the form of powder or sponge, as a traumatic cover and artificial eardrum in the form of a membrane or nonwoven fabric, and as contact lenses in a shaped form. It is also used in a molded form containing a medicine for slow release preparations. In these applications collagen is used in solid form. However, there are other fields in which use of collagen in a fluid solution state is desired. For example, there has been a demand for an aqueous solution of collagen that can be injected into ruptured tissues, for example, through a syringe needle to fill up the affected area without incision. In this case it is necessary that the collagen solution remain fluid during injection without forming fibrous structure, and that the collagen molecules contained in it become oriented into fiber form when exposed to, and equilibrated with, biological conditions after injection to produce bundles of collagen fiber. If such an aqueous solution of collagen be developed, the bundles of collagen fiber formed in living bodies will accept entry of cells and minute blood vessels from the surrounding tissue, and will maintain its volume for a sufficient period of time, thus aiding in filling up the injured part.

Use of soluble collagen or atelocollagen is indispensable to the preparation of a collagen solution having such properties. Collagen of these types is soluble in a dilute acid solution with a pH value of 5 or lower, but such an acidic solution cannot be applied to living bodies. For a collagen solution to be applicable to living bodies, preferably it has properties close to biological conditions, namely, a pH value of about 7 and an osmolality of about 280~290 mOsm/KgH$_2$O, and is preferably capable of being injected, for example, through a fine syringe needle. The acidic collagen solution mentioned above, however, tends to produce collagen fiber before injection under the conditions close to those in living bodies described above, and cannot be applied, for example, through a fine syringe needle.

OBJECTS AND SUMMARY OF THE INVENTION

Thus an object of this invention is to provide an aqueous solution of atelocollagen useful as a medical material, which remains fluid under the pH and osmolality conditions close to those in living bodies as described above and which forms collagen fiber when it becomes equilibrated with biological conditions, for example, when it is injected into living bodies.

Another object of this invention is to provide a method of preparing such an aqueous solution of atelocollagen which comprises adding a pH- and osmolality-adjusting agent to a solution of atelocollagen in an aqueous acid, said adjusting agent being preferably a phosphate buffer or a combination of a phosphate buffer with glucose.

DETAILED DESCRIPTION OF THE INVENTION

The aqueous solution of atelocollagen of this invention has a pH value ranging from about 6.5 to about 8.0 and an osmolality in the range from about 250 to about 320 mOsm/KgH$_2$O.

A phosphate buffer solution selected from the group consisting of combinations, KH$_2$PO$_4$—K$_2$HPO$_4$, KH$_2$PO$_4$—Na$_2$HPO$_4$ and NaH$_2$PO$_4$—Na$_2$HPO$_4$, may be used as an agent to adjust the pH of the aqueous atelocollagen solution of this invention within the range between about 6.5 and about 8.0. The preferable concentration of the phophate buffer in the atelocollagen solution is in the range from 0.09 to 0.12M. If the buffer concentration is adjusted within this range, the osmolality of the atelocollagen solution will be nearly equal to that in living bodies. In addition, other solutes may be added to the atelocollagen solution to adjust osmolality within the range specified above, and glucose was found to be the most preferable solute for this purpose.

It was proved that addition of glucose causes no regeneration of collagen fiber in the atelocollagen solution.

For example, the osmolality of an aqueous atelocollagen solution with its pH controlled at 7.3 by a phosphate buffer of 0.05M concentration was 140 mOsm/KgH$_2$O. No regeneration of collagen fiber was observed in this solution when its osmolality was increased to 306 mOsm/KgH$_2$O by addition of glucose to 3% concentration, or increased to 251 mOsm/KgH$_2$O by addition of glulcose to 2% concentration. In all of these cases, the atelocollagen solution could be injected into living bodies through a fine syringe needle without any trouble, and became equilibrated with biological conditions after injection, regenerating collagen fiber.

The aqueous solution of atelocollagen of this invention can be prepared by dissolving atelocollagen in an aqueous acid solution with a pH value of preferably 4.5 or lower, most preferably, in the range from 3.0 to 4.0, and adjusting the pH of the resulting solution in the range from about 6.5 to about 8.0 and its osmolality in the range from about 250 to about 320 mOsm/KgH$_2$O, by addition of a pH- and osmolality-adjusting agent.

The concentration of atelocollagen in said aqueous acid solution may be in the range from 0.2 to 10%, preferably from 1 to 8%.

As examples of said acid solution may be mentioned aqueous solutions of inorganic and organic acids, such as hydrochloric, acetic, citric and lactic acids, but an aqueous solution of hydrochloric or acetic acid is most preferable.

As the pH- and osmolality-adjusting agent may be used a phosphate buffer solution selected from the group consisting of combinations, $KH_2PO_4$—$K_2HPO_4$, $KH_2PO_4$—$Na_2HPO_4$ and $NaH_2PO_4$—$Na_2HPO_4$. The concentration of these phosphate buffer solutions before addition may be 0.10M or higher, preferably in the range from 0.1 to 0.6M. The preferable mixing ratio of said phosphate buffer solution and said acidic solution of atelocollagen is such that the concentration of the former after mixing will be in the range from 0.09 to 0.12M. It is important that the osmolality of the resulting solution be as close to that in living bodies as possible. If an above-mentioned phosphate buffer solution of 0.10M concentration is used, the osmolality of the resulting solution will be 280 mOsm/KgH$_2$O, a level very similar to that in living bodies.

In addition to the above-specified phosphate buffer solution, the aqueous atelocollagen solution of this invention may include other solutes as osmolality adjusting agent. The most preferable solute used for this purpose is glucose. This solute must be added in such an amount as to give an osmolality in the range from 250 to 320 mOsm/KgH$_2$O to the final solution. For example, it was demonstrated that glucose must be added to 3% concentration when a 0.05M phosphate buffer solution is used, and to 4% concentration when a 0.025M buffer solution is employed. When glucose is used in combination with a phosphate buffer solution, it is preferable to first add glucose to the acidic atelocollagen solution, mix the solution well, and then add the phosphate buffer solution, followed by thorough mixing.

The water, phosphate buffer solution and glucose used for the preparation of the aqueous atelocollagen solution of this invention are all pyrogen-free. To this end purified water obtained by reverse osmosis or double-distillation process commonly used may be employed.

The following examples will further illustrate the present invention.

EXAMPLE 1

A portion of the skin was peeled off from the back of a calf, its periphery was cut out, the remainder was washed with tap water to remove dirt and dust from the surface, and finally washed with pyrogen-free water. The calf hide thus obtained was immersed in 70% ethanol, and all hair and the uppermost surface of the skin were then sliced off with a razor blade, taking care not to leave any hair roots and to keep the exposed surface clean. The back surface was also treated in the same way, thus isolating a clean piece of calf derma. This was immersed in 70% ethanol overnight, excess ethanol was removed and the derma was pulverized under germ-free condition. It was then washed with pyrogen-free, 5% aqueous NaCl solution, dehydrated by centrifugation, washed with pyrogen-free water, and immersed in 70% ethanol overnight. The excess alcohol was centrifugally removed, the resultant powder of derm was put in a germ-free dissolver, and a solution of pepsin in pyrogen-free water, freed from germs by filtration, was added. The amount of pepsin added was 0.5% relative to the powdered derma on dry basis. The concentration of powdered derm was adjusted to about 0.5%, pH was cotrolled at 3 with hydrochloric acid, and the mixture was held at 20° C. for three days with mild stirring to completely dissolve the insoluble collagen of the derma. The atelocollagen solution thus obtained was successively passed through three filters having pore size of 1 $\mu$m, 0.65 $\mu$m and 0.45 $\mu$m, respectively, and the pH of the filtrate was raised to 11.0 by addition of caustic soda solution to deactivate the pepsin. The pH of the resulting solution was then adjusted to 7.0 by addition of hydrochloric acid, the precipitated atelocollagen was collected with a centrifugal separator and washed with pyrogen-free water, the precipitate was again dissolved in pyrogen-free hydrochloric acid, and the pH of the resulting solution was adjusted to 7 to precipitate atelocollagen. The germ- and pyrogen-free product thus obtained was dissolved in a pyrogen-free hydrochloric acid of pH 3.0 to a concentration of 3%.

To 100 parts by weight of this atelocollagen solution was added 50 parts by weight of 0.3M $KH_2PO_4$—$Na_2HPO_4$ buffer solution (pH 7.4). The atelocollagen solution thus prepared was germ- and pyrogen-free and contained 2% atelocollagen, with its buffer solution concentration, pH and osmolality being 0.1M, 7.3 and 280 mOsm/KgH$_2$O, respectively. This solution caused no precipitation of collagen fiber when allowed to stand at room temperature, and could be easily passed through a fine syringe needle. When mixed with a 0.9% NaCl solution (physiological saline solution) or equilibrated with biological conditions, it became turbid at once as a result of collagen fiber formation. This is indicative of the suitability of this solution for injection application.

EXAMPLE 2

A 5% atelocollagen solution of pH 3 was prepared using germ- and pyrogen-free atelocollagen obtained as precipitate in the same way as in Example 1. To 100 parts (by weight) of this solution was added 50 parts by weight of 12%, pyrogen-free aqueous solution of glucose, followed by addition of 50 parts by weight of 0.2M, pyrogen-free $NaH_2PO_4$—$Na_2HPO_4$ buffer solution (PH 7.4). This operation was performed under germ-free condition. The 2.5% atelocollagen solution thus prepared contained 0.05M $NaH_2PO_4$—$Na_2HPO_4$ and 3% glucose, with its pH and osmolality being 7.25 and 306 mOsm/KgH$_2$O, respectively.

This solution caused no precipitation of collagen fiber and could be easily passed through a fine syringe needle. When mixed with a 0.9% physiological saline solution or exposed to biological conditions, it became turbid at once as a result of collagen fiber formation. This is indicative of the suitability of this solution for injection application.

EXAMPLE 3

A 6% atelocollagen solution with its pH controlled to 3 with hydrochloric acid was prepared using the germ- and pyrogen-free atelocollagen obtained in Example 1. Under germ-free condition, 50 parts (by weight) of 4% aqueous glucose solution was added to 100 parts by weight of the atelocollagen solution obtained above, followed by addition of 50 parts by weight of 0.32M $KH_2PO_4$—$K_2HPO_4$ buffer solution. The resultant solution contained 1% glucose and 0.080M buffer solution, and showed a pH value of 7.30. This neutral atelocollagen solution caused no precipitation of collagen fiber at room temperature, and could be easily passed through a fine syringe needle. It regenerated collagen fiber when mixed with a physiological saline solution or exposed to biological conditions, indicating that it is suitable for injection application.

What is claimed is:

1. An aqueous atelocollagen solution comprising dissolved atelocollagen, having a pH in the range from about 6.5 to about 8.0 and an osmolality in the range from about 250 to about 320 mOsm/Kg$H_2O$.

2. An aqueous atelocollagen solution as defined in claim 1 containing, as pH- and osmolality-adjusting agent, a phosphate buffer solution selected from the group consisting of combinations, $KH_2PO_4$—$K_2HPO_4$, $KH_2PO_4$—$Na_2HPO_4$ and $NaH_2PO_4$—$Na_2HPO_4$.

3. An aqueous atelocollagen solution as defined in claim 1 containing, as pH- and osmolality-adjusting agent, glucose and a phosphate buffer solution selected from the group consisting of combinations, $KH_2PO_4$—$K_2HPO_4$, $KH_2PO_4$—$Na_2HPO_4$ and $NaH_2PO_4$—$Na_2HPO_4$.

4. A method of preparing aqueous atelocollagen solution, which comprises dissolving atelocollagen in an aqueous acidic solution and adding, to the resulting solution, a pH- and osmolality-adjusting agent in such an amount as to give a pH value in the range from about 6.5 to about 8.0 and an osmolality from about 250 to about 320 mOsm/Kg$H_2O$.

5. A method of preparing aqueous atelocollagen solution as defined in claim 4 wherein said pH- and osmolality adjusting agent is a phosphate buffer solution selected from the group consisting of combinations, $KH_2PO_4$—$K_2HPO_4$, $KH_2PO_4$—$Na_2HPO_4$ and $NaH_2PO_4$—$Na_2HPO_4$.

6. A method of preparing aqueous atelocollagen solution as defined in claim 4, wherein said pH- and osmolality-adjusting agent comprises glucose and a phosphate buffer selected from the group consisting of combinations, $KH_2PO_4$—$K_2HPO_4$, $KH_2PO_4$—$Na_2HPO_4$ and $NaH_2PO_4$—$Na_2HPO_4$.

7. An aqueous atelocollagen solution as defined in claim 1 which is capable of being injected into living bodies through a fine syringe needle.

8. An aqueous atelocollagen as defined in claim 1 which is capable of passing through a filter having a pore size of 0.45 microns.

* * * * *